United States Patent [19]

Pagano et al.

[11] 3,966,552

[45] June 29, 1976

[54] DEVICE FOR MAKING A CULTURE OF MICRO-ORGANISMS

[75] Inventors: Joseph F. Pagano, Paoli; Ronald J. Schoengold, Thorndale, both of Pa.

[73] Assignee: SmithKline Corporation, Philadelphia, Pa.

[22] Filed: Apr. 14, 1975

[21] Appl. No.: 567,696

[52] U.S. Cl............................ 195/139; 195/103.5 R
[51] Int. Cl.²........................................... C12B 1/02
[58] Field of Search................. 195/139, 127, 103.5

[56] References Cited
UNITED STATES PATENTS

| 3,589,983 | 6/1971 | Holderith et al.................... | 195/139 |
| 3,616,265 | 10/1971 | Pagano .............................. | 195/139 |

*Primary Examiner*—Alvin E. Tanenholtz
*Attorney, Agent, or Firm*—Smith, Harding, Earley & Follmer

[57] ABSTRACT

A device for making a culture of micro-organisms has a container having an open end and means to seal the open end of the container. A second seal divides the container into a first compartment for a liquid culture medium remote from the open end of the container and a second compartment adjacent the open end of the container. A removable elongated member in the container has a portion extending through the second compartment and into said first compartment and removably engaging the second seal to seal liquid culture medium in the first compartment. A culture medium secured to a portion of said elongated member lies in the second compartment. Preferably the sides edges of the elongated member are tapered adjacent its inner end and a portion of the elongated member in the second compartment carries one or more solid culture mediums. Advantageously the second seal member is tapered to guide the elongated member through the center thereof.

7 Claims, 7 Drawing Figures

DEVICE FOR MAKING A CULTURE OF MICRO-ORGANISMS

BACKGROUND OF THE INVENTION

Devices for making a culture of micro-organisms having a culture medium which can be brought directly into contact with a specimen and then returned to a sealed container for growing micro-organisms picked up are known to the art as is seen, for example, in the disclosure of U.S. Pat. No. 3,616,265, issued Oct. 26, 1971. Such devices have as their intended purpose providing office diagnosis within 24 hours without the necessity for a laboratory. In these devices the culture medium is in a solid form secured to a paddle or the like. The term solid as used herein is intended to connote a material which is capable of retaining its shape when secured to a culture paddle. The disclosure of U.S. Pat. No. 3,616,265 is incorporated herein by reference.

This invention increases the versatility of such a device by including means to contain a liquid culture medium in a compartment separated from the compartment containing the solid culture medium. This is highly advantageous, since desirably the culture medium for some micro-organisms such as, for example, trichomonas vaginalis is in liquid form. Thus, for example, it is highly desirable to have a culturing device containing a liquid culture medium for trichomonas vaginalis along with a solid culture medium for Candida (Monilia) for differential diagnosis of vaginal infections.

SUMMARY OF THE INVENTION

A device for making a culture of micro-organisms has a container having an open end and means to seal the open end of the container. A second seal divides the container into a first compartment for a liquid culture medium remote from the open end of the container and a second compartment adjacent the open end of the container. A removable elongated member in the container has a portion extending through the second compartment and into said first compartment and removably engaging the second seal to seal liquid culture medium in the first compartment. A culture medium secured to a portion of said elongated member lies in the second compartment. Preferably the side edges of the elongated member are tapered adjacent its inner end and a portion of the elongated member in the second compartment carries one or more solid culture mediums. Advantageously the second seal member is tapered to guide the elongated member through the center thereof.

DETAILED DESCRIPTION

Figure 1:
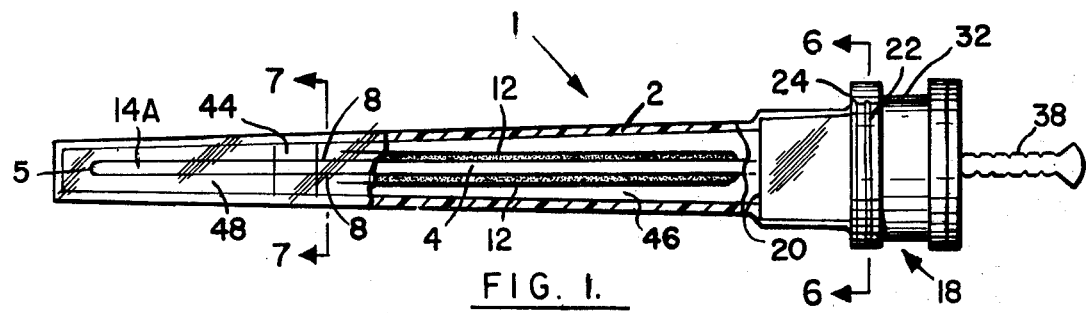
FIG. 1 is an elevational view of a device of the invention.
Figure 2:
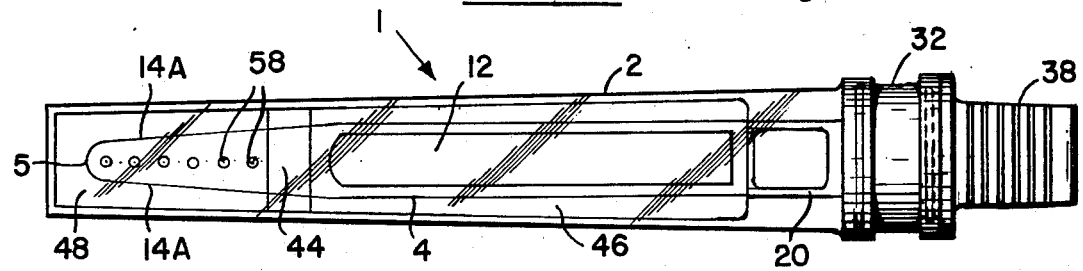
FIG. 2 is a top plan view of the device of FIG. 1.
Figure 3:
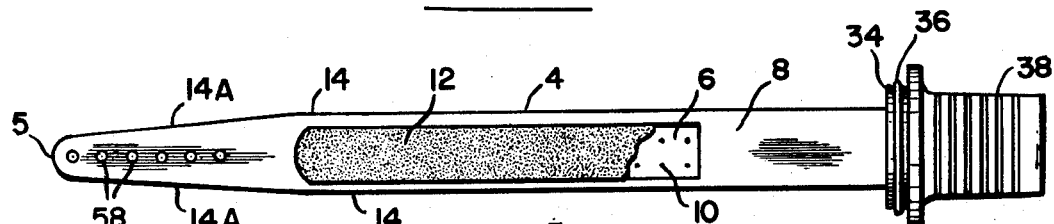
FIG. 3 is a top plan view of the culture paddle of the device of FIG. 1 removed from its container.

Referring now to FIG. 1, a device 1 for making a culture of micro-organisms in accordance with the invention has a transparent container 2 of, for example, glass or a plastic such as an acrylic resin such as methyl methacrylate or a polycarbonate resin. An elongated member 4 has an inner end 5 and a recessed portion 6 in each of the opposed substantially flat faces 8. Each recessed portion 6 is intermediate the ends of the elongated member 4 and has multiple small protrusions 10 (FIG. 3) to facilitate the retention of a body 12 of a solid culture medium in the recessed portions.

Figure 6:
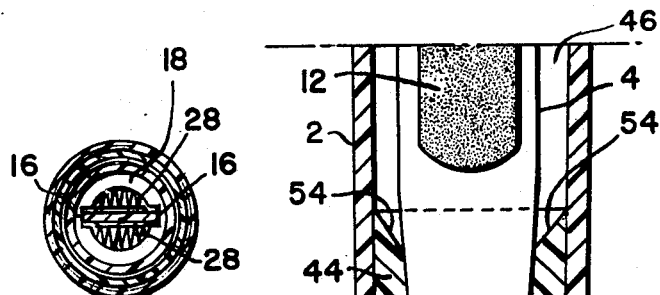
FIG. 6 is a vertical section taken on the plane indicated by the line 6—6 in FIG. 1.
Figure 7:
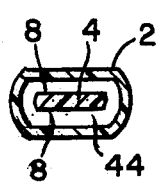
FIG. 7 is a vertical section taken on the plane indicated by the line 7—7 in FIG. 1.

The side edges 14 of elongated member 4 are guided by opposed grooves 16, 16 (FIG. 6) in hollow guide member 18 which has a cylindrical portion 20 (FIG. 1) provided with ridges 22 which sealingly engage a cylindrical entrance portion 24 of container 2. The inner end of guide member 18 has a pair of opposed brush members 28, 28 (FIG. 6) positioned adjacent grooves 16, 16 so as to engage elongated member 4 as it is inserted into container 2.

Guide member 18 has a cylindrical entrance portion 32 which is engaged by a plug portion 34 (FIG. 3) of member 4 having a peripheral ridge 36 to seal closed the end of guide member 18. The outer end of elongated member 4 is in the form of a handle 38.

Figure 4:
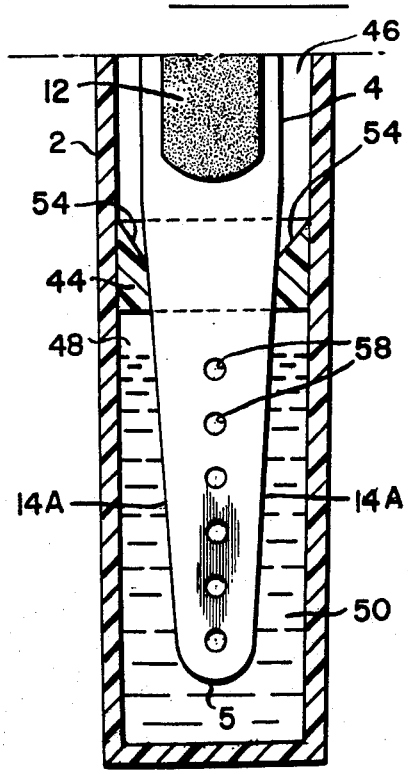
FIG. 4 is a sectional view of the lower end of the device of FIG. 1 taken in the plane of the culture paddle.
Figure 5:
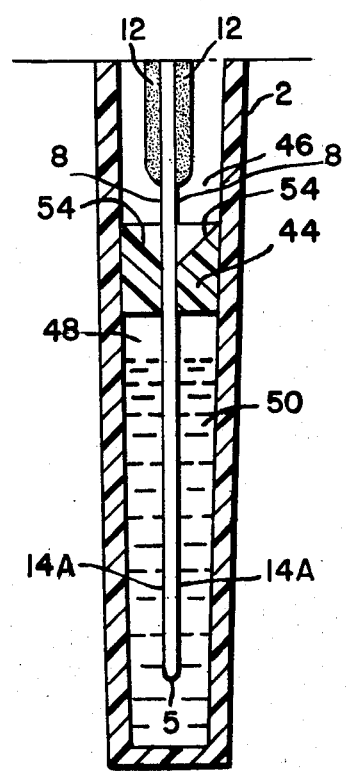
FIG. 5 is a sectional view of the lower end of the device of FIG. 1 taken in a plane transverse to the plane of the culture paddle and partially broken away.

A resilient ring seal 44 is secured inside container 2 by a pressed fit forming a tight seal between the ring seal 44 and the inner wall of container 2. Ring seal 44 divides the interior of the container into a compartment 46 and a compartment 48, the latter compartment containing a liquid culture medium 50 (FIG. 4). The upper end of ring seal 44 as viewed in FIGS. 4 and 5 has an inwardly tapering inner wall 54 to guide the elongated member 4 when it is inserted through the ring member 44. The insertion of the elongated member 4 through guide member 44 is facilitated by the tapered end portions 14A, 14A of side edges 14, 14 of elongated member 4. The elongated member 4 is passed through ring seal 44 until the side edges 14, 14 and the opposed flat faces 8, 8 are in tight engagement with ring seal 44 precluding the escape of liquid culture medium 50 past ring seal 44 into chamber 46. Ring seal 44 is made of a resilient material advantageously a resilient plastic such as, for example, polyethylene or polypropylene.

The elongated member 4 (FIG. 4) is provided with a multiplicity of small openings 58 for the reception of micro-organisms on their walls and the subsequent reception of the liquid culture medium 50.

The liquid culture medium will be one suitable for the micro-organism involved by way of example, if the micro-organism is trichomonas vaginalis a liquid culture medium of the following composition would be used:

| | |
|---|---|
| Trypticase Peptone | 15.0 Gm./L |
| Yeast Extract | 10.0 Gm./L |
| D-Maltose No. M-2250 | 20.0 Gm./L |
| L-Cysteine-HCl No. C-7880 | 1.0 Gm./L |
| L-Ascorbic Acid | 1.0 Gm./L |
| Oxoid Agar No. 1 | 1.0 Gm./L |
| Water (distilled or deionized) | 900 ml./L |
| Horse serum (heat inactivated) | 100 ml./L |
| Nystatin Soln. (200 μ/ml.) | 10.0 ml./L |
| Colistin Soln. (20 μg./ml.) | 10.0 ml./L |
| Penicillin G. Sod. Soln. (5000 μ/ml.) | 20.0 ml./L |
| Neomycin Sulfate Soln. (200 μg./ml.) | 10.0 ml./L |

-continued

| | |
|---|---|
| Brom Cresol Purple Soln. (0.003%) | 30.0 ml./L |
| Dimethyl Sulfoxide ACS Grade (0.1%) | 1.0 ml./L |

A typical companion solid culture medium for use in the opposed recesses 6, 6, for Candida Albicans (Monilia IV) is the following culture medium:

| | |
|---|---|
| G.C. Agar Base | 36.0 Gm./L |
| Bacto Agar | 10.0 Gm./L |
| Water (distilled or deionized) | 925 ml./L |
| Brom Cresol Purple (0.1% solution) | 30 ml./L |
| Dextrose (25% solution) | 16 ml./L |
| Isovitalex Enrichment (contains 0.1% Dextrose) | 10 ml./L |
| Neomycin Sulfate (400 μg./ml.) | 20 ml./L |

It is convenient to have the above exemplified liquid culture medium and solid culture medium in the same culture device for differential diagnosis of vaginal infections.

OPERATION

In operation, the doctor removes the elongated member 4 by handle 38 from the container 2 while holding the container in a vertical position to retain the liquid culture medium 50 in compartment 48. Assuming, for example, that the culture media are those specifically set forth above by way of example, the doctor can use a sterile swab to obtain a vaginal specimen and swab it onto both sides of the elongated member in the area of the openings 58. He can also use the swab to apply the vaginal specimen to the lower half of the solid culture medium 12 in each recess 6. The elongated member is then reinserted into the vertically held container 2 with the tapered wall 54 and the tapered edges 14A, 14A facilitating the passage of elongated member 4 through ring seal 44 until the elongated member is in tight engagement with ring seal 44. After 24 hours of incubation, the doctor will make an observation through the transparent walls of the container 2 to see if any colonies have grown on the solid culture medium 12. Similarly, in a conventional manner he will read the liquid culture medium for turbidity and color change from blue-green (normal) to yellow (positive) in the manner well known to those skilled in the art.

It will be understood that the above description of a specific embodiment is illustrative and is not intended to be limiting.

We claim:

1. A device for making a culture of micro-organisms comprising:
   a container having an open end,
   means to seal the open end of the container,
   second ring seal means dividing said container into a first compartment for a liquid culture medium remote from the open end of the container and a second compartment adjacent the open end of the container,
   a removable elongated member in the container,
   said elongated member having a portion extending through the second compartment and into said first compartment and removably engaging the second seal means to seal liquid culture medium in the first compartment, and
   a culture medium secured to a portion of said elongated member lying in the second compartment.

2. A device in accordance with claim 1 in which the end of the elongated member remote from the open end of the container is tapered.

3. A device in accordance with claim 1 in which the end of the elongated member remote from the open end of the tube has passages therethrough to receive micro-organisms on the passage walls and to receive the liquid culture medium.

4. A device in accordance with claim 1 in which the end of the elongated member remote from the open end of the container is tapered and in which the end of the elongated member remote from the open end of the tube has passages therethrough to receive micro-organisms on the passage walls and to receive the liquid culture medium.

5. A device in accordance with claim 1 in which a second culture medium different from the first culture medium is secured to the elongated member.

6. A device in accordance with claim 1 in which the inner surface of the ring seal tapers inwardly adjacent the end thereof closest to the open end of the container to guide the elongated member.

7. A device in accordance with claim 1 in which the end of the elongated member remote from the open end of the container is tapered and in which the inner surface of the ring seal tapers inwardly adjacent the end thereof closest to the open end of the container to guide the elongated member.

* * * * *